United States Patent
Shin et al.

(10) Patent No.: US 12,196,541 B2
(45) Date of Patent: Jan. 14, 2025

(54) CALIBRATION METHOD OF OPTICAL COHERENCE TOMOGRAPHY DEVICE AND CAMERA

(71) Applicants: HUVITZ CO., LTD., Anyang-si (KR); OSSVIS CO., LTD., Anyang-si (KR)

(72) Inventors: Seong Hun Shin, Anyang-si (KR); Min Soo Cho, Anyang-si (KR); Dong Won Kim, Anyang-si (KR); Weon Joon Lee, Anyang-si (KR)

(73) Assignees: HUVITZ CO., LTD., Anyang-si (KR); OSSVIS C0., LTD., Anyang-si (KR)

( * ) Notice: Subject to any disclaimer, the term of this patent is extended or adjusted under 35 U.S.C. 154(b) by 170 days.

(21) Appl. No.: 18/079,306

(22) Filed: Dec. 12, 2022

(65) Prior Publication Data
US 2023/0194245 A1    Jun. 22, 2023

(30) Foreign Application Priority Data
Dec. 22, 2021    (KR) .......................... 10-2021-0184969

(51) Int. Cl.
*G01B 11/24*    (2006.01)
*G06T 5/80*    (2024.01)
(Continued)

(52) U.S. Cl.
CPC ............. *G01B 11/2441* (2013.01); *G06T 5/80* (2024.01); *G06T 7/521* (2017.01); *G06T 7/80* (2017.01);
(Continued)

(58) Field of Classification Search
CPC ... A61B 5/0059; A61B 5/0066; A61B 5/0073; A61B 3/185; A61B 3/102; A61B 3/14;
(Continued)

(56) References Cited

U.S. PATENT DOCUMENTS 9,593,933 B2 *    3/2017   Oritz Egea .......... G01B 9/02076
2007/0291277 A1    12/2007  Everett et al.
(Continued)

FOREIGN PATENT DOCUMENTS

KR         10-0939537 B1       2/2010
KR       10-2017-0119820 A    10/2017
KR       10-2023-0084032 A     6/2023

OTHER PUBLICATIONS

Zhang, Z., "A Flexible New Technique for Camera Calibration", Technical Report MSR-TR-98-71, Dec. 2, 1998, last updated on Aug. 13, 2008, Microsoft Research, Microsoft Corporation, One Microsoft Way, Redmond, WA.
Extended European Search Report for counterpart European Application No. 22212548.6, dated May 15, 2023.
Request for the Submission of an Opinion for counterpart Korean Application No. 10-2021-0184969, dated Jul. 3, 2023.

*Primary Examiner* — Hoa Q Pham
(74) *Attorney, Agent, or Firm* — United One Law Group LLC; Kongsik Kim; Jhongwoo Peck

(57) ABSTRACT

A calibration method of an optical coherence tomography (OCT) device and a camera using the same target includes irradiating a shape measurement light to a calibration target, obtaining a surface shape image thereof by detecting light reflected by a surface of the calibration target using a shape measurement camera, and calibrating the surface shape image according to an actual shape of the calibration target; obtaining surface and internal three-dimensional images of the calibration target by scanning with a layer measurement light using the OCT measurement unit, extracting a surface shape image of the calibration target from the three-dimensional images, and calibrating the surface shape image according to the actual surface shape of the calibration target; and matching a calibration image obtained by the shape measurement camera and a surface calibration image obtained by the OCT measurement unit to be displayed at the same spatial coordinates.

3 Claims, 7 Drawing Sheets

(51) Int. Cl.
*G06T 7/521* (2017.01)
*G06T 7/80* (2017.01)

(52) U.S. Cl.
CPC .............. *G06T 2207/10048* (2013.01); *G06T 2207/10101* (2013.01)

(58) Field of Classification Search
CPC ..... A61B 3/0025; A61B 3/0033; A61F 9/007; H04N 13/296; H04N 13/246; H04N 13/156; H04N 13/204; G06T 7/30; G06T 3/0068; G06T 2200/24; G06T 2207/10101; G06T 2207/10012; G06T 2207/30041; A06B 34/30; G01B 9/02091; G01B 9/02089; G01B 9/02072; G01N 21/8422

USPC .................................. 356/479, 497, 601–623
See application file for complete search history.

(56) References Cited

U.S. PATENT DOCUMENTS

| | | | |
|---|---|---|---|
| 2014/0107960 A1* | 4/2014 | Oritz Egea | G06T 5/80 702/104 |
| 2015/0168250 A1* | 6/2015 | Saxer | G01B 9/02064 356/479 |
| 2019/0117075 A1 | 4/2019 | Fan et al. | |
| 2021/0169324 A1 | 6/2021 | Tripathi et al. | |
| 2023/0194238 A1* | 6/2023 | Jeong | G01B 9/02091 356/497 |
| 2023/0263368 A1* | 8/2023 | Brushett | A61B 5/0066 |
| 2024/0302274 A1* | 9/2024 | Hart | G01B 9/02072 |

* cited by examiner (Related Art)

(Related Art)

CALIBRATION METHOD OF OPTICAL COHERENCE TOMOGRAPHY DEVICE AND CAMERA

CROSS-REFERENCE TO RELATED APPLICATION

This application claims benefit of priority to Korean Patent Application No. 10-2021-0184969 filed on Dec. 22, 2021, which is incorporated herein by reference in its entirety.

TECHNICAL FIELD

The present disclosure relates to a calibration method of an optical coherence tomography device and a camera, and more particularly, to a calibration method of an optical coherence tomography device and a camera using the same target.

BACKGROUND

Optical scanners utilizing camera technologies are used to measure predetermined samples, for example, the shape of teeth and tissues in an oral cavity. FIG. 1 is a diagram showing the principle of imaging a sample shape of a conventional camera scanner. As shown in FIG. 1, a conventional camera scanner includes a projector 12 that irradiates measurement light to a sample S such as a tooth; and a camera 14 that obtains a surface shape of the sample S by detecting the light reflected by the sample S. The measurement light (e.g., visible light) emitted from the projector 12 is irradiated to the sample S, and the light reflected by the sample S is detected by the camera 14, thereby acquiring two-dimensional shape information of the surface of the sample S.

In the case of using the camera scanner described above, since the internal state of the sample S cannot be comprehended, a method of obtaining an internal layer image of the sample S by using an optical coherence tomography (OCT) device is known (Refer to Korean Patent Application No. 10-2021-0171392). FIG. 2 is a diagram showing a method of obtaining an internal layer image of a sample S by using a conventional optical coherence tomography (OCT) scanner. As shown in FIG. 2, a conventional optical coherence tomography (OCT) scanner includes an OCT measurement unit 22 that transmits measurement light (e.g., near-infrared light) through a sample S, detects reflected light (scattered light) reflected by the surface and each layer on the inside of the sample S, and obtains surface and internal cross-sectional images of the sample S; and an OCT scan probe 24 that irradiates the measurement light emitted from the OCT measurement unit 22 to a desired location on the sample S and transfers the reflected light reflected by the sample S to the OCT measurement unit 22. The OCT measurement unit 22 is a conventional device that obtains layer information on the inside of the sample S by using the coherence properties of measurement light. The OCT scan probe 24 may include a collimator 24a that focuses the measurement light and the reflected light; a reflection mirror 24b that reflects the focused measurement light to a desired measurement location on the sample S and transfers the reflected light reflected by the sample S to the collimator 24a; and an objective lens 24c that focuses the measurement light reflected by the reflection mirror 24b onto a desired imaging location on the sample S.

The spatial coordinates of a three-dimensional image obtained by the OCT measurement unit 22 and the spatial coordinates of a three-dimensional image obtained by the structured light-based camera 14 device do not generally coincide but have different spatial coordinates. Therefore, in order to obtain more reliable external surface and internal images for the same sample S, it is necessary to adjust the images so that the three-dimensional image obtained by the OCT measurement unit 22 and the three-dimensional image obtained by the structured light-based camera 14 device match each other.

PRIOR ART LITERATURE

Korean Patent Application No. 10-2021-0171392

SUMMARY

It is an object of the present disclosure to provide a method of calibrating an optical coherence tomography (OCT) device and a camera so that the spatial coordinates of a three-dimensional image obtained by the optical coherence tomography device and the spatial coordinates of a three-dimensional image obtained by the camera device match each other.

It is another object of the present disclosure to provide a calibration method of an optical coherence tomography device and a camera that can obtain more reliable external surface and internal images for the same sample S.

In order to achieve the above objects, the present disclosure provides a calibration method of a combined device, wherein the combined device comprises a shape measurement light projector 12 configured to irradiate shape measurement light; a shape measurement camera 14 configured to obtain a surface shape image of a target T by detecting reflected light formed by the shape measurement light being reflected by a surface of the target T; and an optical coherence tomography (OCT) measurement unit 22 configured to transmit layer measurement light through the target T, detect reflected light reflected by the surface and internal layers of the target T, and obtain surface and internal cross-sectional images of the target T, the calibration method comprising:

irradiating the shape measurement light to a calibration target T, obtaining a surface shape image of the calibration target T by detecting the reflected light formed by the shape measurement light being reflected by the surface of the calibration target T by using the shape measurement camera 14, and calibrating the surface shape image of the calibration target T obtained by the shape measurement camera 14 according to an actual shape of the calibration target T; obtaining surface and internal three-dimensional images of the calibration target T by scanning the calibration target T with the layer measurement light by using the OCT measurement unit 22, extracting a surface shape image of the calibration target T from the three-dimensional images, and calibrating the surface shape image of the calibration target T obtained by the OCT measurement unit 22 according to the actual surface shape of the calibration target T; and matching a calibration image obtained by the shape measurement camera 14 and a surface calibration image obtained by the OCT measurement unit 22 so as to be displayed at the same spatial coordinates.

According to the calibration method of an optical coherence tomography device and a camera in accordance with the present disclosure, a combined device of the optical coherence tomography device and the camera can be calibrated so that the spatial coordinates of a three-dimensional image obtained by the optical coherence tomography (OCT) device and the spatial coordinates of a three-dimensional image obtained by the camera device match each other.

DETAILED DESCRIPTION

Figure 1:
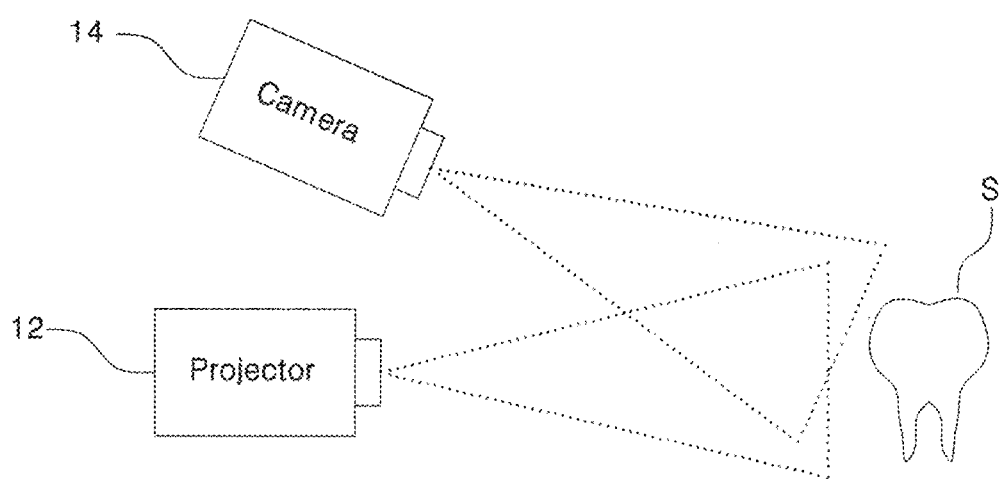
FIG. 1 is a diagram showing the principle of imaging a sample shape of a conventional camera scanner.
Figure 2:
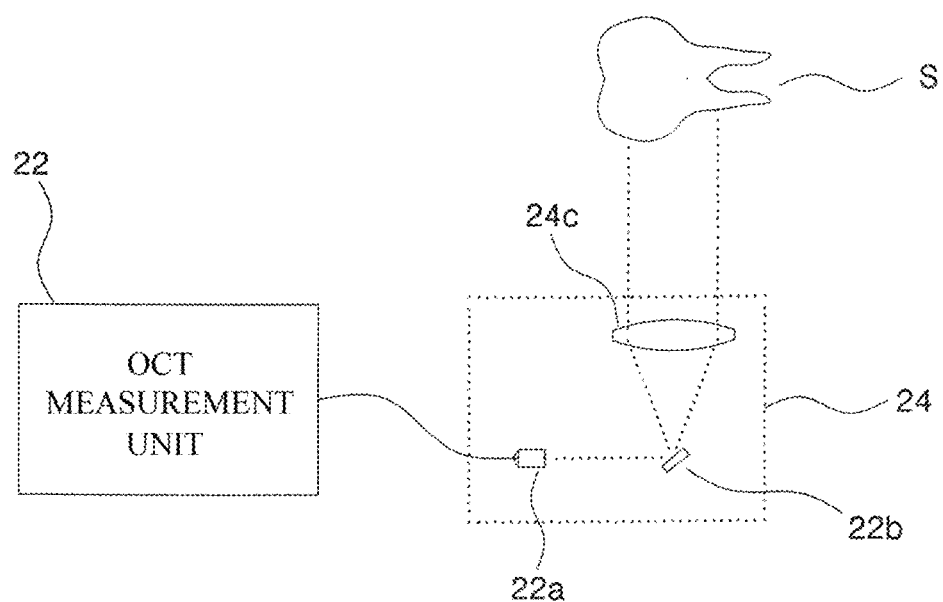
FIG. 2 is a diagram showing a method of obtaining an internal layer image of a sample S by using a conventional optical coherence tomography (OCT) scanner.

Hereinafter, the present disclosure will be described in detail with reference to the accompanying drawings. In the accompanying drawings, the same reference numerals are assigned to elements performing the same or similar functions as those of the prior art.

Figure 3:
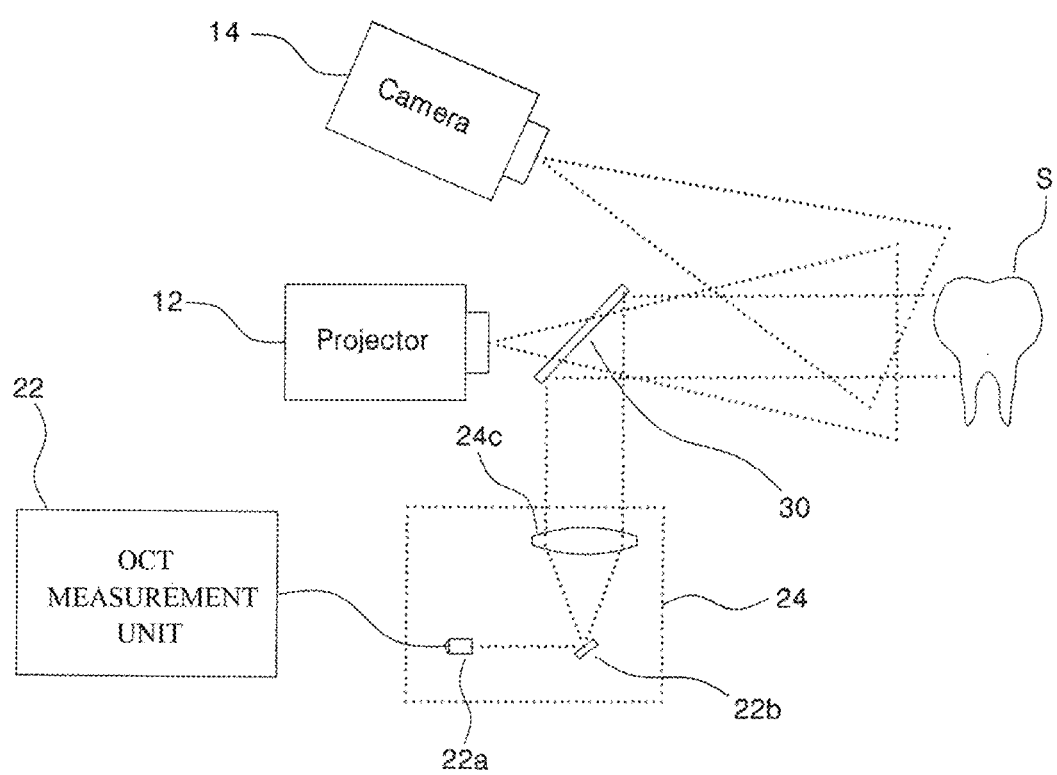
FIG. 3 is a diagram showing the configuration of a combined device to which a calibration method of an optical coherence tomography device and a camera in accordance with the present disclosure can be applied.

FIG. 3 is a diagram showing the configuration of a combined device to which a calibration method of an optical coherence tomography (OCT) device and a camera in accordance with the present disclosure can be applied. As shown in FIG. 3, a combined device to which a calibration method in accordance with the present disclosure can be applied may include a shape measurement light projector 12, a shape measurement camera 14, and an optical coherence tomography (OCT) measurement unit 22, and may further include an OCT scan probe 24 and a beam splitter 30 as necessary. The shape measurement light projector 12 irradiates shape measurement light for obtaining a shape image of a target T. As the shape measurement light, any measurement light that can obtain a shape image of the target T may be used without limitation, and preferably visible light, e.g., visible light having a wavelength of 400 to 700 nm may be used. The shape measurement camera 14 is a device that obtains a surface shape image of the target T by detecting reflected light formed by the shape measurement light being reflected by the surface of the target T, and includes a conventional image sensor. In operation, the shape measurement light is outputted from the shape measurement light projector 12, the outputted shape measurement light passes through the beam splitter 30 and then irradiates the target T, and the reflected light reflected by the target T is detected by the shape measurement camera 14, thereby obtaining a surface shape image of the target T. At this time, the two-dimensional image of the target T obtained by the shape measurement camera 14 may be converted into a three-dimensional image using a triangulation method or the like.

The OCT measurement unit 22 is a device that transmits layer measurement light (e.g., near-infrared light) through the target T, detects reflected light (scattered light) reflected by the target T, specifically, the surface and the internal layers of the target T, and obtains surface and internal cross-sectional images of the target T, and is a conventional device that obtains layer information inside an object by using the coherence properties of the layer measurement light. For example, the layer measurement light may be broadband low-coherence light having a short coherence distance, and preferably be near-infrared light, specifically, near-infrared light having a wavelength of 750 to 1500 nm. The OCT scan probe 24 is a device that irradiates the layer measurement light emitted from the OCT measurement unit 22 to a desired location on the target T, and transfers the reflected light reflected by the target T to the OCT measurement unit 22. The OCT scan probe 24 may include a collimator 24a that focuses the layer measurement light and its reflected light; a reflection mirror 24b that reflects the focused layer measurement light onto a desired imaging location on the target T and transfers the reflected light reflected by the target T to the collimator 24a; and an objective lens 24c that focuses the measurement light reflected by the reflection mirror 24b onto a desired imaging location on the target T. Here, as the reflection mirror 24b, a micro-electro-mechanical system (MEMS) mirror that enables the imaging locations on the target T to be scanned in sequence by adjusting the reflection angle of the layer measurement light may be used. For example, the reflection mirror 24b may rotate based on two axes (e.g., x-axis and y-axis in an orthogonal relationship) and sequentially scan the plane on which the target T is located, and the layer measurement light may be irradiated inside the target T in a direction perpendicular to the plane (z-axis direction, orthogonal to the x-axis and y-axis), thereby obtaining a three-dimensional layer image of the target T.

The beam splitter 30 is a device that separates the optical paths of the shape measurement light emitted from the shape measurement light projector 12 and of the layer measurement light emitted from the OCT scan probe 24, and separates a shape acquisition optical system formed by the shape measurement light projector 12 and the shape measurement camera 14 from a layer acquisition optical system formed by the OCT measurement unit 22 and the OCT scan probe 24. For example, as shown in FIG. 3, the beam splitter 30 may be a dichroic mirror 20 that transmits the shape measurement light emitted from the shape measurement light projector 12 and reflects the layer measurement light emitted from the OCT scan probe 24, thereby irradiating the target T with the shape measurement light and the layer measurement light, and separates and transfers each reflected light to the shape measurement camera 14 and the OCT measurement unit 22. Therefore, the beam splitter 30 allows both the external surface shape image and the internal layer image of the target T to be obtained by irradiating the target T with the shape measurement light and the layer measurement light by superimposing them with each other.

Figure 4:
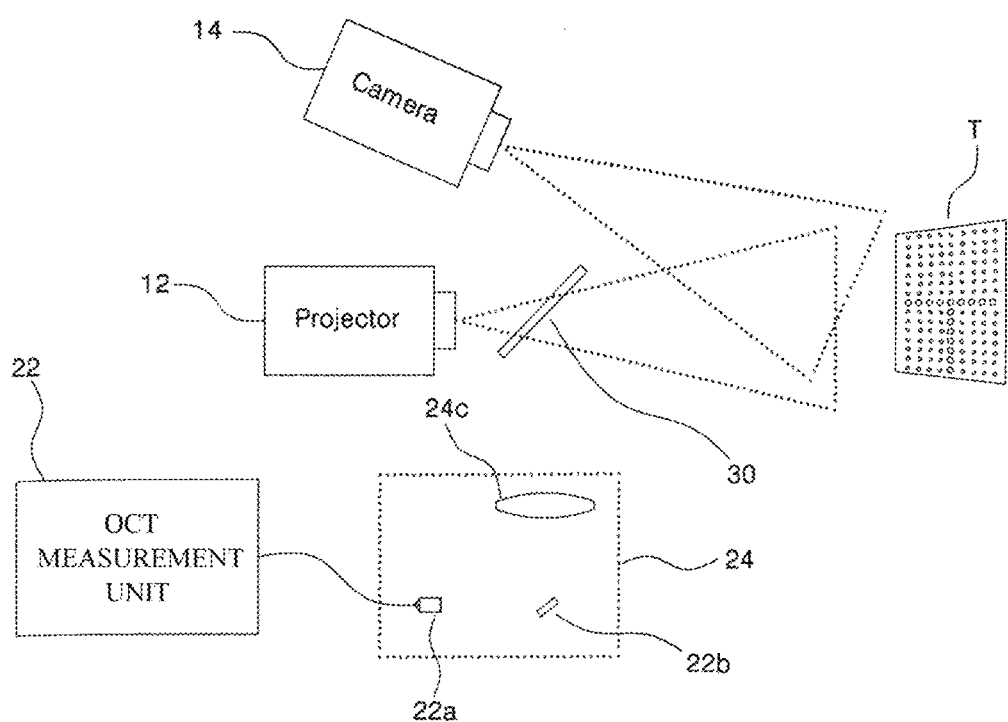
FIGS. 4 to 7 are diagrams for describing a calibration method of an optical coherence tomography device and a camera in accordance with the present disclosure.
Figure 5:
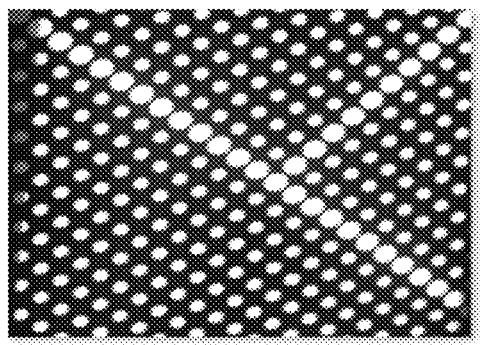
Figure 5:
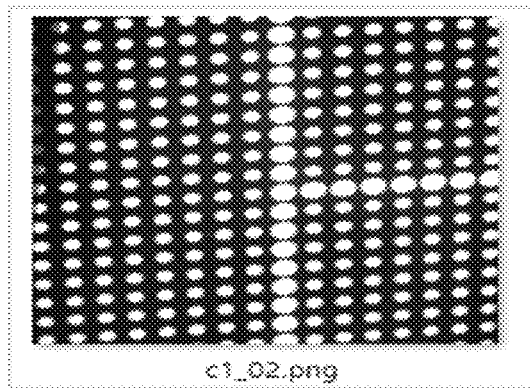
Figure 5:
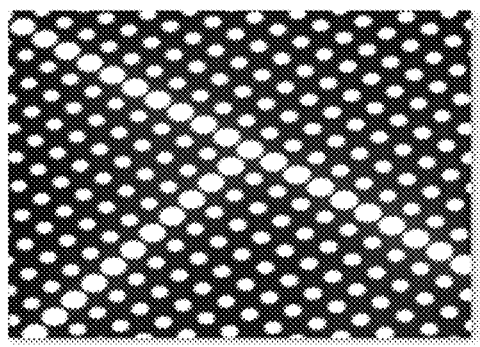
Figure 5:
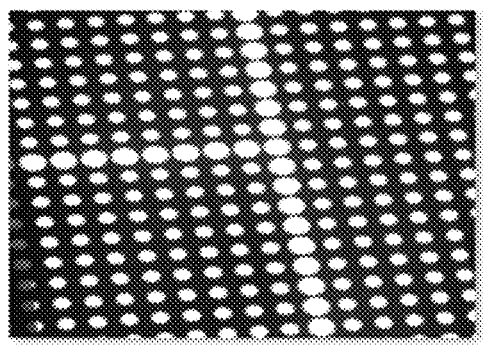

FIGS. 4 to 7 are diagrams for describing a calibration method of an optical coherence tomography device and a camera in accordance with the present disclosure. In order to carry out the calibration of the optical coherence tomography device and the camera according to the present disclosure, first, as shown in FIG. 4, the shape measurement light is irradiated onto the calibration target T by using the shape measurement light projector 12, a surface shape image of the calibration target T is obtained by detecting reflected light formed by the shape measurement light being reflected by the surface of the calibration target T by using the shape measurement camera 14, the surface shape image of the calibration target T obtained by the shape measurement camera 14 is calibrated according to the actual shape of the calibration target T. The calibration target T may be a standard target having a pattern of a predetermined shape formed on the surface thereof, and preferably, may be a non-transmissive planar target having a pattern of a predetermined shape (e.g., a dot shape or a checkerboard pattern) uniformly formed on the surface thereof. FIG. 5 is a view showing an example of a surface shape image of the calibration target T obtained by the shape measurement camera 14 in this way. As shown in FIG. 5, surface shape images of various forms are obtained according to the locations or directions in the calibration target T. Since the shape measurement camera 14 is composed of various optical elements such as lenses and image elements, certain distortions occur in the images obtained by the shape measurement camera 14 depending on the characteristics of the optical elements and the image elements. On the other hand, since the surface shape image of the calibration target T, specifically, the position of the pattern formed on the surface of the calibration target T is known in advance, this can be used to correct, i.e., calibrate the distortions of the surface shape image of the calibration target T obtained by the shape measurement camera 14. Such calibration of the camera 14 is a process of obtaining distortion coefficients according to the locations of an image, and may be performed according to a conventional method (Reference: A Flexible New Technique for Camera Calibration, https://www.microsoft.com/en-us/research/wp-content/uploads/2016/02/tr98-71.pdf).

Figure 6:
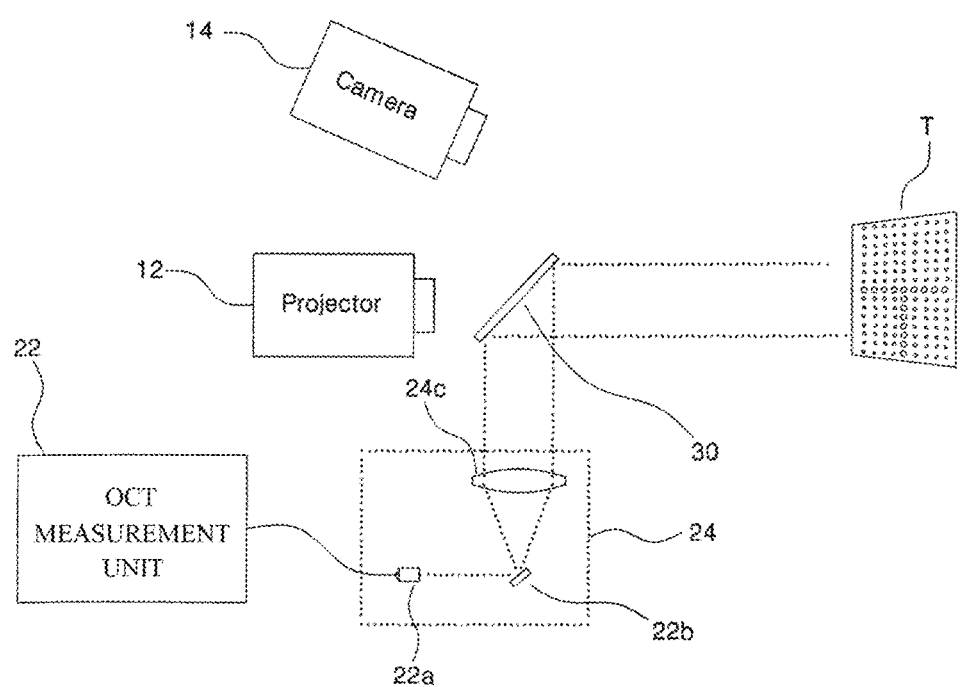
Figure 7:
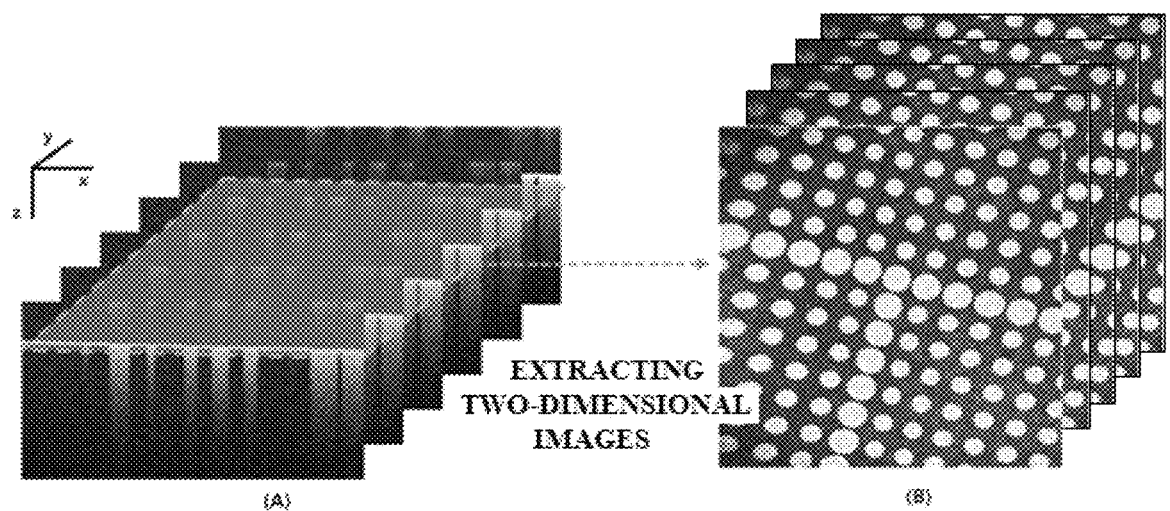

Next, as shown in FIG. 6, surface and internal three-dimensional images of the calibration target T are obtained by scanning the calibration target T with the layer measurement light by using the OCT measurement unit 22 and the OCT scan probe 24, a surface shape image of the calibration target T is extracted from the three-dimensional images (surface detection), and the surface shape image of the calibration target T obtained by the OCT measurement unit 22 is calibrated according to the actual surface shape of the calibration target T. The surface image calibration in the OCT measurement unit 22 may be performed in the same manner as the image calibration of the camera 14 described above. FIG. 7 is a view showing an example of the three-dimensional image (A of FIG. 7) of the calibration target T obtained by the OCT measurement unit 22 as described above and the two-dimensional surface shape image (B of FIG. 7) extracted therefrom. As shown in FIG. 7, for example, if the calibration target T is a non-transmissive planar target on which a predetermined pattern of dot shapes is formed uniformly on the surface thereof, a three-dimensional image in which a surface image is clear but an internal image is relatively opaque is obtained as shown in A of FIG. 7, and if a two-dimensional surface shape image is extracted from this, a two-dimensional image corresponding to the surface shape image of the calibration target T obtained by the shape measurement camera 14 can be obtained as shown in B of FIG. 7, and this can be used to carry out image calibration of the OCT measurement unit 22.

After completing the calibration of the shape measurement camera 14 and the OCT measurement unit 22 in this way, the calibration image obtained by the shape measurement camera 14 and the surface calibration image obtained by the OCT measurement unit 22 are matched so as to be displayed at the same spatial coordinates. In other words, since the shape measurement camera 14 and the OCT measurement unit 22 each have positional information on the same point in the same calibration target T, the image obtained by the shape measurement camera 14 and the image obtained by the OCT measurement unit 22 are made to be displayed at the same location in one image by transforming, for example, by rotating or enlarging or reducing, the images obtained by the shape measurement camera 14 and the OCT measurement unit 22 so that they are displayed at the same location in one image.

According to the present disclosure, a combined image can be obtained for the same calibration target T by calibrating the surface shape image obtained by the shape measurement camera 14, extracting and calibrating the surface image from the three-dimensional image obtained by the OCT measurement unit 22, and then matching these images, i.e., matching the spatial coordinates of the two images.

Although the present disclosure has been described with reference to the accompanying drawings and illustrative embodiments in the above, the present disclosure is not limited to what is shown in the drawings and the embodiments described above. In the following claims, reference numerals are indicated to aid understanding, but the scope of the following claims should not be limited to what is shown by the reference numerals and in the drawings and should be construed to encompass all modifications, and equivalent constructions and functions of the illustrative embodiments.

The invention claimed is:

1. A calibration method of a combined device, the calibration method comprising:
   irradiating shape measurement light to a calibration target (T);
   obtaining a first surface shape image of the calibration target (T) by detecting reflected light formed by the shape measurement light being reflected by a surface of the calibration target (T) by using a shape measurement camera;
   calibrating the first surface shape image of the calibration target (T) obtained by the shape measurement camera according to an actual shape of the calibration target (T);
   obtaining surface and internal three-dimensional images of the calibration target (T) by scanning the calibration target (T) with layer measurement light by using an optical coherence tomography (OCT) device, wherein the calibration target (T) is a non-transmissive planar target having a pattern of a predetermined shape uniformly formed on a surface thereof, such that a surface image that is clear and an internal image that is more opaque than the surface image are obtained as the three-dimensional images of the calibration target (T) by the OCT device;
   extracting a second surface shape image of the calibration target (T), wherein the second surface shape image is obtained as a two-dimensional image extracted from the three-dimensional images;
   calibrating the second surface shape image of the calibration target (T) obtained by the OCT device according to the actual surface shape of the calibration target (T); and
   matching a first calibration image obtained by the shape measurement camera and a second calibration image obtained by the OCT device so as to be displayed at the same spatial coordinates.

2. The calibration method of claim 1, wherein the matching the first calibration image obtained by the shape measurement camera and the second calibration image obtained by the OCT device transforms the images, so that the image obtained by the shape measurement camera and the image obtained by the OCT device are displayed at the same location in one image.

3. The calibration method of claim 1, wherein the shape measurement light is visible light, and the layer measurement light is near-infrared light.

* * * * *